United States Patent
Czech et al.

[11] Patent Number: 5,785,985
[45] Date of Patent: Jul. 28, 1998

[54] MEDICAL PRESSURE-SENSITIVE ADHESIVE MASS HAVING A HIGH MOISTURE VAPOR TRANSMISSION AND A HIGH ADHESIVE STRENGTH ON DRY HUMAN SKIN AND IN CASE OF INTENSE PERSPIRATION

[75] Inventors: Zbigniew Czech, Koblenz; Kurt Seeger, Neuwied, both of Germany

[73] Assignee: Lohmann GmbH & Co., KG, Neuwied, Germany

[21] Appl. No.: 737,899

[22] PCT Filed: May 5, 1995

[86] PCT No.: PCT/EP95/01723

§ 371 Date: Nov. 13, 1996

§ 102(e) Date: Nov. 13, 1996

[87] PCT Pub. No.: WO95/31224

PCT Pub. Date: Nov. 23, 1995

[30] Foreign Application Priority Data

May 13, 1994 [DE] Germany .................. 44 16 928.0

[51] Int. Cl.$^6$ ........................................ A61F 13/02
[52] U.S. Cl. ........................................ 424/448; 424/449
[58] Field of Search ........................................ 424/448, 449

[56] References Cited

U.S. PATENT DOCUMENTS

| | | | |
|---|---|---|---|
| 4,721,748 | 1/1988 | Iovine | 524/460 |
| 5,057,179 | 10/1991 | Dulaney et al. | 156/280 |
| 5,346,957 | 9/1994 | Tsuji | 525/122 |

FOREIGN PATENT DOCUMENTS

| | | |
|---|---|---|
| 61-290956 | 12/1986 | Japan . |
| 62-091577 | 4/1987 | Japan . |
| 3-068672 | 3/1991 | Japan . |
| 3-162473 | 7/1991 | Japan . |
| 2 070 631 | 9/1981 | United Kingdom . |
| 84/0383 | 10/1984 | WIPO . |

*Primary Examiner*—D. Gabrielle Phelan
*Attorney, Agent, or Firm*—Wenderoth, Lind, & Ponack, L.L.P.

[57] ABSTRACT

A medical pressure sensitive adhesive mass having a moisture vapor transmission of at least 10,000 g/m$^2$/24.h (measured with a pressure sensitive adhesive film having a weight of 30 g/m$^2$) and an excellent adhesion to both dry skin and that is moist due to perspiration, comprising:

A) a copolymer synthesized from components comprising:
  1) 50 to 95%-wt., preferably 70 to 90%-wt., based on the weight of the copolymer, of one or several alkyl esters of acrylic and/or methacrylic acid have 4 to 12 C-atoms in the alkyl residue; and
  2) 5 to 50%-wt., preferably 10 to 30%-wt., based on the weight of the copolymer, of a vinylcarboxylic acid, B) 25 to 90%-wt., preferably 50 to 80%-wt., of a hydrophilic emulsifier comprising tertiary or quaternary ammonium groups, C) 15 to 60%-wt., preferably 20 to 40%-wt., of a hydrophilic polyoxyalkylene groups-containing emulsifier which is free from amino groups, D) 1 to 20%-wt., preferably 3 to 15%-wt., of a polyvinylcarboxylic acid, E) 1 to 15%-wt., preferably 3 to 10%-wt., of a tackifying resin, and F) 0.05 to 5%-wt., preferably 0.1 to 2%-wt., of a crosslinking agent. The medical pressure sensitive adhesive mass is useful as sweat insensitive occlusive dressing, highly permeable wound dressings and medical adhesive tapes.

25 Claims, No Drawings

5,785,985

MEDICAL PRESSURE-SENSITIVE ADHESIVE MASS HAVING A HIGH MOISTURE VAPOR TRANSMISSION AND A HIGH ADHESIVE STRENGTH ON DRY HUMAN SKIN AND IN CASE OF INTENSE PERSPIRATION

This application is a 371 of PCT/EP95/01723, filed May 5, 1995.

BACKGROUND OF THE INVENTION

The present invention relates to medical pressure-sensitive adhesive masses having a high moisture vapor transmission (MVT) of at least 10,000 g/m²/24.h (measured according to the inverted cup method at 40° C. and 80% Δ r.h. using a pressure-sensitive adhesive film having a weight of 30 g/m²) and an excellent adhesion to dry and freely perspiring skin. The present invention further relates to their production and use.

Medical pressure-sensitive adhesive masses having a high MVT and a high adhesive force on skin that is moist owing to heavy perspiration have been known for some time. However, these pressure-sensitive adhesive masses have some disadvantages limiting their practical use to a great extent.

The state of the art in this field may be described as follows:

U.S. Pat. No. 5,057,179 describes a polar dispersion based on polyvinyl acetate, which has a good adhesion to moist substrates.

JP-A 31 62473 describes a pressure-sensitive adhesive mass with adhesion to moist surfaces. This pressure-sensitive adhesive mass consists of an acrylate copolymer built-up of alkyl acrylate, alkylene alkoxyacrylate, and vinylcarboxylic acid, and an ethylene vinyl acetate copolymer.

JP-A 30068672 includes adhesive tapes for medical patches adhering to moist or dry skin. These products comprise silicone pressure-sensitive adhesive masses and water-soluble carboxyvinyl polymers, cellulose derivatives or starch derivatives.

JP-A 62091577 describes pressure-sensitive adhesive masses with a marked adhesion to dry and moist substrates, the adhesion to moist substrates being achieved by introduction of water absorbing agents based on cross-linked polyacrylate salts.

JP-A 61290956 describes resins for medical pressure-sensitive adhesive masses composed of acrylamide derivatives, (meth)acrylates, and glycol acrylic-acid esters.

WO 84013837 describes pressure-sensitive adhesive masses especially suitable for moist skin; these are based on copolymers of hydrophobic acrylates, hydrophobic vinyl polyethers, and polar monomers. (Meth)acrylic acid, itaconic acid, (meth)acrylamide, or n-vinyl pyrrolidone are used as a polar monomer.

GB-A 2070631 describes copolymers of butyl acrylate, ethylhexyl acrylate, and acrylic acid, for the use in medical products. In addition of cohesive properties, these copolymers have an adhesion to dry and moist skin and a vapor permeability of more than 300 g/m²/24.h.

The prior art includes pressure-sensitive adhesive masses of differing compositions; they adhere to dry and moist skin but their adhesive power in case of heavy perspiration is reduced to such an extent that they cannot be used for patches.

The physiological acceptability of the employed raw materials has been of major importance in many pressure-sensitive adhesive masses classified as being suitable for medical purposes; but the MVT in adhesive medical products, also called breathability, has been left out of consideration. However, this is important for both protection of the skin from maceration, which results from moisture accumulation under the adhesive mass, and permanent adhesion to the skin, which is also impaired by moisture accumulation.

There is only scanty information about the MVT-values of prior art pressure-sensitive adhesive masses. From their chemical composition it can be concluded that they are insufficient for the application in case of intense perspiration. For example, the value of 300 g/m²/24 h given as "lower limit" for the MVT in GB-A 2070631, is absolutely insufficient even in case of minor perspiration.

Test experience has shown that the MVT-values achievable with known pressure-sensitive adhesive masses are in the range of 1,000 to 8,000 g/m²/24.h in case of pressure-sensitive adhesive layers having a weight per unit area of about 30 g/m²; this value is sufficient in some cases, however, is considered in need of improvement. Owing to their chemical composition, the known medical pressure-sensitive adhesive masses can frequently only hardly be modified with respect to increasing the MVT. For example, the addition of hydrophilic portions often results in a drastic decrease of the adhesive strength when used on human skin, because partial swelling of the hydrophilic components takes the adhesive components off the skin.

SUMMARY OF THE INVENTION

Starting from this state of the art, it is the object of the present invention to provide medical pressure-sensitive adhesive masses which do not show the aforementioned disadvantages and have an MVT of at least 10,000 g/m²/24.h (with a film weight of 30 g/m²) with an excellent adhesion to both dry skin and skin that is moist because of heavy perspiration.

Most surprisingly, this object has been achieved with the following composition of the medical pressure-sensitive adhesive mass that comprises:

A) a copolymer synthesized from the components:
  1) 50 to 95%-wt., preferably 70 to 90%-wt. of one or several alkyl esters of acrylic and/or methacrylic acid having 4 to 12 C-atoms in the alkyl residue and
  2) 5 to 50%-wt., preferably 10 to 30%-wt. of a vinylcarboxylic acid, relative to the copolymer B) 25 to 90%-wt., preferably 50 to 80%-wt. of a hydrophilic emulsifier comprising tertiary or quaternary ammonium groups, C) 15 to 60%-wt., preferably 20 to 40%-wt. of a hydrophilic, polyoxyalkylene groups-containing emulsifier which is free from amino groups, D) 1 to 20%-wt., preferably 3 to 15%-wt. of a polyvinylcarboxylic acid, E) 1 to 15%-wt., preferably 3 to 10%-wt. of a tackifying resin, and F) 0.05 to 5%-wt., preferably 0.1 to 2%-wt. of a cross-linking agent.

DETAILED DESCRIPTION OF THE INVENTION

The medical pressure-sensitive adhesive mass according to the present invention consists of copolymers synthesized from tackifying alkyl esters of (meth)acrylic acid having 4 to 12 C-atoms in the alkyl residue and vinylcarboxylic acid(s), which, after synthesis, are modified with the remaining components B to F to form the finished pressure-sensitive adhesive masses.

The pressure-sensitive adhesive mass according to the present invention will be illustrated in greater detail in the following:

The pressure-sensitive adhesive properties of the polyacrylate pressure-sensitive adhesive masses can be influenced by the choice of the tackifying monomers. The alkyl esters of acrylic and/or methacrylic acid having 4 to 12 C-atoms in the alkyl residue originate from the group consisting of n-butyl, isobutyl, tert-butyl, pentyl, hexyl, heptyl, octyl, isooctyl, 2-ethylhexyl, 2-methyl heptyl, nonyl, decyl, and isodecyl acrylate and/or methacrylate; n-butyl acrylate and 2-ethylhexyl acrylate being preferred.

To introduce carboxyl groups into the polymer chains, vinylcarboxylic acids are used as comonomers, they are selected from (meth)acrylic acid, β-acryloyloxypropionic acid, dimethyl acrylic acid, trichloroacrylic acid, vinylacetic acid, fumaric acid, crotonic acid, aconitic acid, or itaconic acid. Acrylic acid and β-acryloyloxypropionic acid are preferred as particularly suitable vinylcarboxylic acids.

Further hydrophilic groups are attached by admixing a hydrophilic emulsifier comprising tertiary or quaternary ammonium groups and having an HLB-value (hydrophilic-lipophilic balance) of 10 to 20. Ethoxylated amines, such as N,N',N'-tris(2-hydroxyethyl)-N-tallow-1,3-diaminopropane and tallow-propylenediaminopolyglycol ether, have proved to be particularly suitable.

Moreover, the addition of a hydrophilic, polyoxyalkylene groups-containing emulsifier which is free from amino groups proves advantageous, without affecting the adhesive force to dry skin and skin that is moist because of perspiration. Polyoxyalkylenes, such as polyethylene glycols or polypropylene glycols having a molecular weight between 200 and 10,000, are preferably used as hydrophilic emulsifiers which are free from amino groups. Polyethylene glycol 400 and polyethylene glycol 600 have proved to be particularly suitable.

To allow easy and gentle removal of coated medical pressure-sensitive adhesive masses in the form of patches from the skin, tackifying resins are used. Hydrogenated or partially hydrogenated hydrocarbon resins and hydrogenated or partially hydrogenated derivatives of abietinic acid in amounts of up to 15%-wt. have proved to be particularly suitable for this purpose.

To provide the polyacrylate pressure-sensitive adhesive masses with an acceptable structural strength, cross-linkers reacting with carboxyl groups are used; for example, metal chelates, metallic acid esters, epoxide, aziridine, or triazine resins. Metal chelates, such as, aluminum, hafnium, titanium, zirconium, or iron acetyl-acetonate have proved to be particularly suitable. Polytitanic acid esters, for example, polybutyl titanate, are preferred among the metallic acid esters.

If the copolymer can be produced by conventional solution polymerization, esters of saturated carboxylic acids (e.g., ethyl acetate), aliphatic hydrocarbons (e.g., n-heptane), aliphatic ketones (e.g., acetone or methyl ethyl ketone), special boiling-point spirits, or the mixtures of these solvents, may be used as solvents. Usually used radical starters include azo compounds, such as, 2,2'-azobis-(2,4-dimethylpentanitrile), 2,2'-azobis-(2-methylpropanenitrile), 2,2'-azobis-(2-methylbutanenitrile), or 1,1'-azobis-(cyclohexanecarbonitrile); or peroxides, such as, di-benzoyl peroxide.

According to a process for the production of the medical pressure-sensitive adhesive mass, the copolymer A) is synthesized from components 1) and 2) and mixed with the other components B) to F), the weight percentage of all components A)–F) totaling 100%-wt.

Another subject matter of the present invention is the use of the medical pressure-sensitive adhesive masses according to the present invention for the production of sweat-insensitive occlusive dressings, wound dressings which are highly permeable to water vapor, and medical adhesive tapes used in sports medicine. If required, these medical products can be sterilized by means of steam, γ-irradiation, or gassing with ethylene oxide.

The medical pressure-sensitive adhesive mass according to the present invention stands out for an extremely high MVT which is on the level of above 28,000 $g/m^2/24.h$. It has a good adhesion to dry and profusely sweating skin. It can be removed from the skin in a gentle and soft manner, there are no skin irritations or allergids. These pressure-sensitive adhesive masses are most suitable to tackify several medical products, such as sweat-insensitive occlusive dressings, wound dressings which are highly permeable to water vapor, and medical adhesive tapes used in sports.

The medical products produced with the pressure-sensitive adhesive masses according to the present invention were evaluated by physico-technical tests, such as MVT, and by testing the adhesive force (peel adhesion) to steel plates according to AFERA 4001. Testing the adhesive strength to the intact skin of five test persons was carried out by applying strips of 2.5 cm in width to the hairless undersurface of the lower arms, and measuring the adhesive strength after 10 min. and after 3 hours, following the standard of AFERA 4001. In this connection, further assessment criteria included skin tolerance and residue-free removal. The statistical evaluation showed that products with the pressure-sensitive adhesive masses according to the present invention adhered to human skin without any problems, did not cause significant skin irritations, and could be removed without any residues.

The present invention will be illustrated in greater detail with reference to the following examples:

EXAMPLE 1:

200 g copolymer solution, polymerized from 80 g n-butyl acrylate and 20 g acrylic acid in 100 g ethyl acetate, having an average molecular weight of 600,000 dalton, is mixed at room temperature with 70 g tallow-propylenediaminopolyglycol ether, 30 g polyethylene glycol 400, 15 g polyacrylic acid having an average molecular weight of 400,000 dalton, 6 g of the glycerol ester of dihydroabietinic acid, and 1 g aluminum acetylacetonate.

The pressure-sensitive adhesive mass so obtained is spread at different layer thicknesses on a siliconized polyester film using a coating bar, and is then dried at 100° C. for 30 min. in a drying cabinet to form pressure-sensitive adhesive films of the thickness a) 20 μm b) 30 μm c) 40 μm The pressure-sensitive adhesive films are transfer-laminated on a polyurethane film having a thickness of 25 μm and an MVT of 40,000 $g/m^2/24.h$. The examination (cf. Table 1) was carried out in comparison with a commercial competitive product d) having a pressure-sensitive adhesive film of 30 μm in thickness. In addition to the physico-technical tests, a wearing test over 24 hours using 5×7 cm-sections is carried out. Whereas skin maceration, caused by moisture accumulation under the adhesive film, is observed in the competitive product, the test persons' skin under the sections coated with the pressure-sensitive adhesive mass according to the present invention is completely dry.

TABLE 1

Examination of the adhesive mass of Example 1 as compared to the comparative product

|  | unit | a) | b) | c) | d) = competitor |
|---|---|---|---|---|---|
| thickness of PUR-film | μm | 30 | 30 | 30 | 30 |
| thickness of adh. film | μm | 20 | 30 | 40 | 30 |
| MVT | g/m²/24 · h | 35,000 | 30,000 | 23,000 | 5,000 |
| adhesive strength AFERA 4001 | N/25 mm | 6.0 | 8.3 | 9.5 | 7.5 |
| adh. strength skin[1] | N/25 mm |  |  |  |  |
| Test person 1 |  | 1.8/2.5 | 2.2/2.8 | 2.5/2.9 | 2.2/1.8[2] |
| Test person 2 |  | 0.9/2.0 | 1.3/2.3 | 1.5/2.5 | 1.1/0.9 |
| Test person 3 |  | 1.5/2.2 | 2.3/2.5 | 2.5/3.2 | 2.0[3] |
| Test person 4 |  | 2.0/2.8 | 2.3/3.2 | 2.4/3.3 | 2.4/1.2 |
| Test person 5 |  | 1.5/1.9 | 2.3/2.4 | 2.5/3.0 | 1.9/2.0[2] |

[1] First values measured after 10 min., the second ones after 3 hours
[2] adhesive residues on the skin
[3] came off too early In comparison with the competitive product it can be seen that the level of adhesive strength is nearly the same in the measurement after 10 min. The efficiency of the novel pressure-sensitive adhesive becomes apparent in the measurement after 3 hours. While the adhesive force of the competitive product decreases in most test persons, and partially is even insufficient for permanent adhesion, the adhesive strength of the pressure-sensitive adhesive mass according to the present invention increases in most cases. Looking at the MVT-values, the explanation is found: in the competitive product they are clearly below those of the pressure-sensitive adhesive mass according to the present invention.

Examples 2 to 15 were carried out in accordance with Example 1.

The exact composition of the starting materials for the production of the medical pressure-sensitive adhesive masses according to the present invention can be seen in Table 2, the test results using pressure-sensitive adhesive films of 30 μm in thickness are summarized in Table 3.

The abbreviations used in the Tables are listed in the following.

List of abbreviations:

Table 2:

2-EHA—2-ethylhexyl acrylate

AlACA—aluminum acetylacetonate

AA—acrylic acid

APA—β-acryloyloxypropionic acid

BA—butyl acrylate

HCR—hydrocarbon resin

GEDA—glycerol ester of dihydroabietinic acid

HfACA—hafnium acetylacetonate

PAA—polyacrylic acid

PBT—polybutyl titanate

PEG 400—polyethylene glycol with a molecular weight of 400

PEG 600—polyethylene glycol with a molecular weight of 600

PEG-DME 500—polyethylene glycol dimethyl ether with a molecular weight of 500

THTD—N,N',N'-tris(2-hydroxyethyl)-N-tallow-1,3-diaminopropane

TPD—tallow-propylenediaminopolyglycol ether

Table 3:

MVT—moisture vapor transmission of a pressure-sensitive adhesive film (weight: 30 g/m²), measured according to the inverted-cup method, calculated according to the formula $$\frac{1}{MVT_{ges}} = \frac{1}{MVT_{PUR\text{-}film}} + \frac{1}{MVT_{adhesive}}$$

AF—adhesive force AFERA 4001
AF-TP—adhesive force on the skin of test person No.

TABLE 2[1]

Composition in Examples 2–15

| | copolymer of | | | additives | | | | | | | | | | |
|---|---|---|---|---|---|---|---|---|---|---|---|---|---|---|
| | alkyl(meth) acrylate | | vinyl- carboxylic acid | ammonium groups-containing emulsifier | | polyoxyalkylene groups-containing emulsifier | | | polyvinyl carboxylic acid | resin | | cross-linking agent | | |
| Example | BA | 2-EHA | AA | APA | THTD | TPD | PEG400 | PEG600 | PEG-DME 500 | PAA | GEDA | HCR | AlACA | PBT | HfACA |
| 2 | 50 | 40 | 10 | — | 60 | — | — | 16 | — | 1 | 3 | — | 3 | — | — |
| 3 | — | 80 | 20 | — | 70 | — | 17 | — | — | 15 | 5 | — | — | 2 | — |
| 4 | 85 | — | — | 15 | — | 50 | — | — | 30 | 5 | — | 10 | 1 | — | — |
| 5 | — | 93 | 7 | — | 20 | 35 | — | — | 25 | 3.5 | — | 5 | — | — | 1.5 |
| 6 | — | 95 | 5 | — | 25 | — | — | 15 | 10 | 4 | 6.5 | — | 0.5 | — | — |
| 7 | 90 | — | 5 | 5 | — | 35 | 30 | — | — | 10 | — | 4.5 | — | — | 2.5 |
| 8 | — | 90 | — | 10 | 40 | — | — | 40 | — | 2 | 4 | — | — | — | 1 |
| 9 | — | 84 | — | 16 | 50 | — | — | — | 20 | 4.2 | 5 | — | — | 0.8 | — |
| 10 | 55 | 15 | 30 | — | — | 80 | — | 30 | — | 6 | — | 8 | 0.3 | 0.2 | — |
| 11 | 85 | — | 15 | — | 20 | 50 | — | — | 25 | 7 | 3 | 3 | 2 | — | — |
| 12 | 91 | — | 9 | — | — | 75 | 10 | 20 | — | 4 | 6 | — | — | 4 | — |
| 13 | — | 80 | — | 20 | 55 | — | 27 | — | — | 5 | — | 3 | — | — | 5 |
| 14 | — | 95 | — | 5 | — | 65 | — | 35 | — | 6 | 10 | — | — | 3 | — |
| 15 | 60 | 15 | 25 | — | 15 | 15 | 25 | — | — | 4.5 | — | 6 | 2.5 | — | — |

[1] all indications given in %-wt.

TABLE 3

Test result of the pressure-sensitive adhesive masses of Examples 2–15

| Examination | unit | pressure-sensitive adhesive mass produced according to Example ... | | | | | | |
|---|---|---|---|---|---|---|---|---|
| | | 2 | 3 | 4 | 5 | 6 | 7 | 8 |
| MVT | g/m²/24 · h | 32,000 | 30,000 | 38,000 | 35,000 | 28,000 | 36,500 | 30,000 |
| AF | N/25 mm | 8.4 | 6.8 | 8.5 | 9.1 | 7.6 | 7.3 | 7.8 |
| AF-TP 1[1] | N/25 mm | 2.0/2.2 | 2.1/2.4 | 1.6/1.8 | 2.5/3.0 | 1.6/2.1 | 1.7/1.8 | 2.4/1.7 |
| AF-TP 2 | N/25 mm | 1.1/1.5 | 1.6/2.0 | 2.0/1.5 | 3.0/1.6 | 2.0/1.6 | 1.0/1.0 | 1.5/1.6 |
| AF-TP 3 | N/25 mm | 1.6/2.0 | 2.0/2.2 | 2.1/2.8 | 2.2/2.0 | 1.3/1.8 | 1.4/1.6 | 2.1/2.0 |
| AF-TP 4 | N/25 mm | 2.2/2.3 | 2.5/2.8 | 1.9/2.3 | 3.2/3.0 | 1.9/2.3 | 1.5/2.0 | 1.9/1.9 |
| AF-TP 5 | N/25 mm | 1.3/1.8 | 2.0/1.8 | 2.0/2.1 | 2.5/2.8 | 1.8/2.2 | 2.0/1.8 | 1.6/1.7 |

| Examination | unit | 9 | 10 | 11 | 12 | 13 | 14 | 15 |
|---|---|---|---|---|---|---|---|---|
| MVT | g/m²/24 · h | 31,000 | 32,000 | 29,000 | 31,000 | 36,000 | 33,000 | 34,000 |
| AF | N/25 mm | 6.9 | 4.9 | 7.3 | 6.2 | 8.6 | 9.2 | 8.8 |
| AF-TP 1[1] | N/25 mm | 2.6/2.4 | 3.2/3.0 | 3.1/2.6 | 2.8/2.5 | 2.6/2.6 | 1.8/1.9 | 2.0/2.0 |
| AF-TP 2 | N/25 mm | 0.8/1.2 | 0.9/1.3 | 1.6/1.5 | 1.8/2.2 | 1.6/2.1 | 0.9/0.8 | 1.5/2.0 |
| AF-TP 3 | N/25 mm | 2.8/2.6 | 2.5/2.3 | 1.4/1.6 | 1.7/1.7 | 2.0/2.1 | 1.8/2.1 | 1.8/2.0 |
| AF-TP 4 | N/25 mm | 2.5/2.6 | 2.2/1.9 | 1.5/1.9 | 2.0/2.2 | 2.1/2.5 | 1.5/2.1 | 1.8/2.5 |
| AF-TP 5 | N/25 mm | 2.2/2.3 | 1.8/1.8 | 1.4/1.6 | 1.8/1.9 | 1.8/2.0 | 1.6/2.1 | 1.8/1.9 |

[1]Fist values measured after 10 min., second values after 3 hours.

All of the above test results show that the medical pressure-sensitive adhesive mass according to the present invention stands out for an extremely high MVT on a level of above 28,000 g/m²/24.h. They have a good adhesion to both dry skin and profusely perspiring skin. Removal from the skin is gentle and soft, there are no skin irritations or allergids. These pressure-sensitive adhesive masses are most suitable for tackifying many medical products, such as sweat-insensible occlusive dressings, wound dressings that are highly permeable to water vapor, and adhesive tapes used in sports.

We claim:

1. A medical pressure sensitive adhesive mass having a moisture vapor transmission of at least 10,000 g/m²/24.h (measured with a pressure sensitive adhesive film having a weight of 30 g/m²) and an excellent adhesion to both dry skin and that is moist due to perspiration, comprising:

A) a copolymer synthesized from components comprising:
   1) 50 to 95%-wt., based on the weight of the copolymer, of one or several alkyl esters of acrylic and/or methacrylic acid have 4 to 12 C-atoms in the alkyl residue; and
   2) 5 to 50%-wt., based on the weight of the copolymer, of a vinylcarboxylic acid, B) 25 to 90%-wt. of a hydrophilic emulsifier comprising tertiary or quaternary ammonium groups, C) 15 to 60%-wt. of a hydrophilic polyoxyalkylene groups-containing emulsifier which is free from amino groups, D) 1 to 20%-wt. of a polyvinylcarboxylic acid, E) 1 to 15%-wt. of a tackifying resin, and F) 0.05 to 5%-wt. of a cross-linking agent.

2. The medical pressure-sensitive adhesive mass according to claim 1 characterized in that the (meth)acrylic-acid alkyl ester having 4 to 12 C-atoms in the alkyl residue is selected from the group consisting of n-butyl, isobutyl, tert-butyl, pentyl, hexyl, heptyl, octyl, isooctyl, 2-ethylhexyl, 2-methyl heptyl, nonyl, decyl, and isodecyl acrylate and/or methacrylate.

3. The medical pressure-sensitive adhesive mass according to claim 1 characterized in that the hydrophilic emulsifier comprising tertiary or quaternary ammonium groups has an HLB-value of 10 to 20 and is selected from the group consisting of ethoxylated amines.

4. The medical pressure-sensitive adhesive mass according to claim 1 characterized in that the hydrophilic, polyoxyalkylene groups-containing emulsifier which is free from amino groups is selected from the group consisting of aliphatic polyoxyalkylenes having a molecular weight between 200 and 10,000.

5. The medical pressure-sensitive adhesive mass according to claim 1 characterized in that the vinylcarboxylic acid is selected from the group consisting of (meth)acrylic acid, β-acryloyloxypropionic acid, dimethyl acrylic acid, trichloroacrylic acid, vinylacetic acid, fumaric acid, crotonic acid, aconitic acid, or itaconic acid, or mixtures of these acids.

6. The medical pressure-sensitive adhesive mass according to claim 1 characterized in that the polyvinylcarboxylic acid is an un-crosslinkedpolyvinylcarboxylic acid.

7. The medical pressure-sensitive adhesive mass according to claim 6 characterized in that the polyvinylcarboxylic acid is poly- acrylic acid.

8. The medical pressure-sensitive adhesive mass according to claim 1 characterized in that the tackifying resin is selected from the group consisting of hydrogenated or partially hydrogenated hydrocarbon resins and/or the group consisting of hydrogenated or partially hydrogenated derivatives of abietinic acid.

9. The medical pressure-sensitive adhesive mass according to claim 1 characterized in that the cross-linking agent is a metal chelate, metallic acid ester, an epoxide, aziridine, or triazine resin.

10. The medical pressure-sensitive adhesive mass according to claim 1 characterized in that it is sterilized.

11. A process for the production of a medical pressure-sensitive adhesive mass according to claim 1, characterized in that the copolymer A) is synthesized from components 1) and 2) and is mixed with the remaining components B) to F).

12. The medical pressure-sensitive adhesive mass according to claim 1, wherein the copolymer comprises 70 to 90%-wt. of component 1).

13. The medical pressure-sensitive adhesive mass according to claim 1, wherein the copolymer comprises 10 to 30%-wt. of component 2).

14. The pressure-sensitive adhesive mass according to claim 1, wherein component B) is present in an amount of 50 to 80%-wt.

15. The pressure-sensitive adhesive mass according to claim 1, wherein component C) is present in an amount of 20 to 40%-wt.

16. The pressure-sensitive adhesive mass according to claim 1, wherein component D) is present in an amount of 3 to 15%-wt.

17. The pressure-sensitive adhesive mass according to claim 1, wherein component E) is present in an amount of 3 to 10%-wt.

18. The pressure-sensitive adhesive mass according to claim 1, wherein component F) is present in an amount of 0.1 to 2%-wt.

19. The medical pressure sensitive adhesive mass according to claim 1, wherein the copolymer A) comprises 70 to 90%-wt. of component 1) and 10–30%-wt. of component 2), component B) is present in an amount of 50 to 80%-wt., component C) is present in an amount of 20 to 40%-wt., component D) is present in an amount of 3 to 15%-wt., component E) is present in an amount of 3 to 10%-wt., and component F) is present in an amount of 0.1 to 2%-wt.

20. A sweat-insensitive occlusive dressing comprising the medical pressure-sensitive adhesive mass according to claim 1.

21. A sweat-insensitive occlusive dressing comprising the medical pressure-sensitive adhesive mass according to claim 19.

22. A wound dressing, which is highly permeable to moisture vapor, comprising the medical pressure-sensitive adhesive mass according to claim 1.

23. A wound dressing, which is highly permeable to moisture vapor, comprising the medical pressure-sensitive adhesive mass according to claim 19.

24. A medical adhesive tape comprising the medical pressure-sensitive adhesive mass according to claim 1.

25. A medical adhesive tape comprising the medical pressure-sensitive adhesive mass according to claim 19.

* * * * *